US00PP10590P

United States Patent [19]

Cole

[11] Patent Number: Plant 10,590

[45] Date of Patent: Sep. 8, 1998

[54] SUGAR MAPLE 'BARRETT COLE'

[75] Inventor: Robert B. Cole, Circleville, Ohio

[73] Assignee: J. Frank Schmidt & Son Co., Boring, Oreg.

[21] Appl. No.: 781,660

[22] Filed: Jan. 10, 1997

[51] Int. Cl.[6] ..... A01H 5/00

[52] U.S. Cl. ..... Plt./53.6

[58] Field of Search ..... Plt./53.6

[56] References Cited

U.S. PATENT DOCUMENTS

P.P. 4,979 2/1983 Wandell ..... Plt./53.6

P.P. 5,079 8/1983 Wandell ..... Plt./53.6

*Primary Examiner*—James R. Feyrer

*Assistant Examiner*—Kent L. Bell

*Attorney, Agent, or Firm*—Klarquist Sparkman Campbell Leigh & Whinston LLP

[57] ABSTRACT

A sugar maple tree named 'Barret Cole' having a compact growth habit, and a dwarf or semi-dwarf growth rate. My new cultivar has a short internode length and has a narrow upright shape with a straight, dominant leader.

3 Drawing Sheets

DESCRIPTION

The present invention relates to a new and distinct variety of sugar maple tree which I have named 'Barrett Cole'.

I discovered my new tree as a chance seedling growing in a cultivated area in Circleville, Pickaway County, Ohio Although the parentage of my new variety is unknown, it is believed to be a chance seedling of *Acer saccharum.* As I observed the initially discovered tree of my new variety, my attention was drawn to this tree because of its narrow upright shape and compact growth habit.

Observations of my new variety have convinced me that this new tree is truly unique.

Asexual propagation of my new tree has been performed at my direction at a J. Frank Schmidt & Son Co. nursery at Boring, Oreg., by both budding and grafting onto *Acer saccharum* rootstock.

This propagation, and a successive asexual propagations, and observations of the resulting progeny, have proven the characteristics of my new variety of sugar maple tree to be firmly fixed. Furthermore, these observations have confirmed that my new variety represents a new and improved variety of sugar maple tree, as particularly evidenced by the unique combination of a compact growth habit with a narrow upright shape, a straight dominant leader, and short internode length.

The accompanying photographs depict the color of the tree and foliage of my new variety, as well as the shape of the tree, as nearly true as is reasonably possible to make the same in a color illustration of this character.

Figure 1:
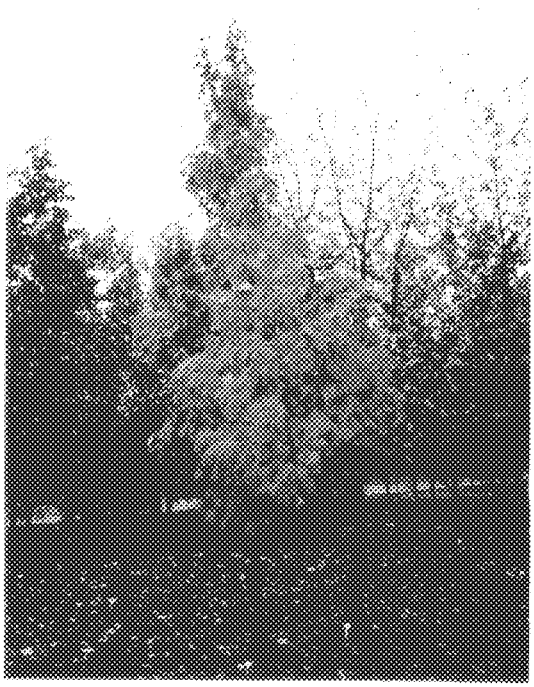
FIGS. 1 and 2 are photographs of trees of my new variety in yellow-orange fall color and show how fall color can vary in the tree.
Figure 2:
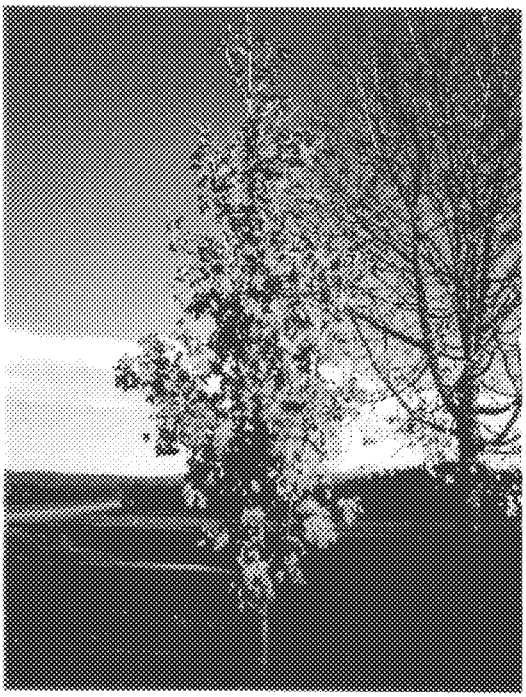
Figure 3:
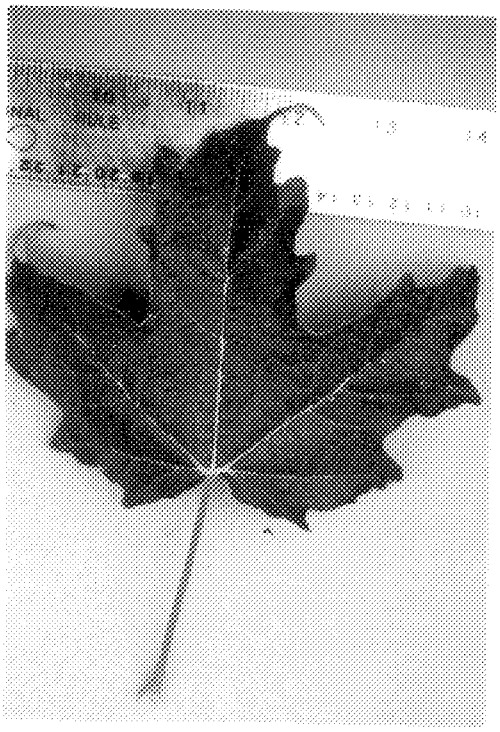
FIG. 3 is a photograph of the upper surface of a leaf from a tree of my new variety in its summer color.
Figure 4:
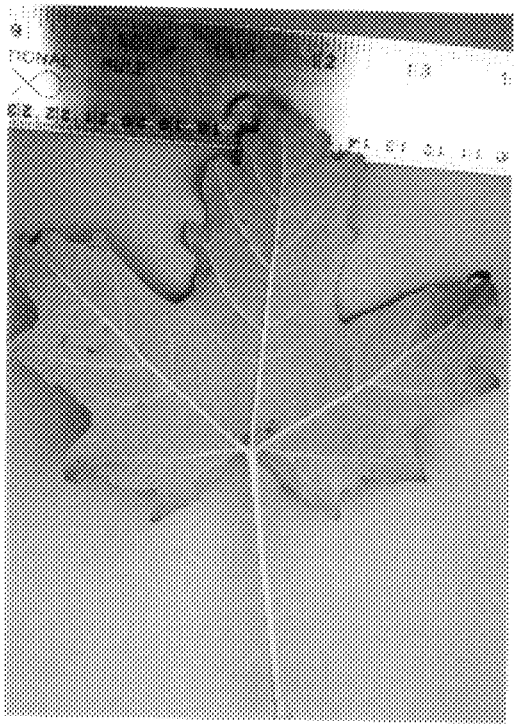
FIG. 4 is a photograph of the underside of a leaf from a tree of my new variety.
Figure 5:
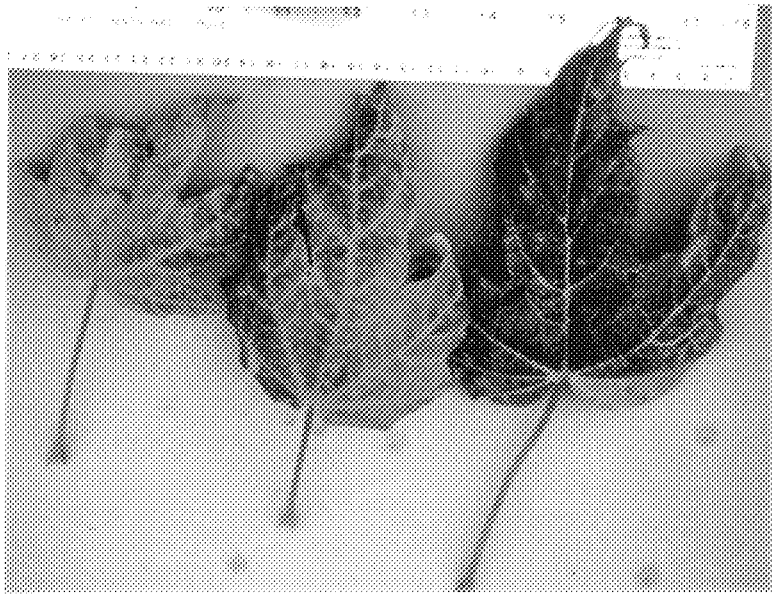
FIG. 5 is a photograph of a group of leaves from a tree of my new variety illustrating orange fall color and the variable leaf sizes.

My 'Barrett Cole' variety has not been observed under all growing conditions and thus variations may occur as a result of different growing conditions. The following is a detailed description of my new variety of sugar maple tree with color terminology in accordance with The Royal Horticultural Society Colour Chart (R.H.S.), published by The Royal Horticultural Society of London. Except for flowers and fruit, the observations are of trees growing in Boring, Oreg.

THE PLANT

Parentage: Chance seedling believed to be of *Acer saccharum* of unknown origin found growing in a cultivated area in Circleville, Pickaway County, Ohio.

Tree Shape: Columnar with strongly ascending branches.

Trunk: Sturdy, straight, round.

Bark: Smooth except for fine vertical fissuring and very slight scaliness.

*Immature bark color.*—Grey-brown R.H.S. 199C.

*Mature bark color.*—Grey-brown R.H.S. 199B.

Branches: Current season branches are short, sturdy, strongly upward in orientation, with a very short internode length. Branch angle at point of attachment to trunk generally about 45° to 70°. In general, the branches curve upwardly and at about one meter from the trunk the branches are angled from about 10° to 15° from vertical. Internode length varies from 25 to 40 mm on vigorously growing branches.

*Immature twig color.*—Yellow-green R.H.S. 146B.

*Mature twig color.*—Greyed-orange R.H.S. 166D.

Leaves: Opposite, entire, palmately lobed. Leaves are deeply cut into three to five palmate lobes. The larger lobes often develop two additional points along their sides, especially when growing under vigorous conditions.

*Base.*—Truncate to cordate.

*Tips.*—Tips of leaf lobes are narrowly acute to acuminate.

*Serrations:* None.

*Pubescence:* Glabrous except for pubescence in the axils of the veins on the underside of the leaf.

*Leaf surface:* Slightly rugose.

*Leaf color:* Upper summer leaf color is green R.H.S. 139A, with the under leaf color being green R.H.S. 136C to 138B. The fall color is a mixture of shades similar to yellow-orange R.H.S. 23B, orange-red R.H.S. 32A, and red R.H.S. 42A.

*Size:* Variable, mature leaves typically 10 to 18 cm wide by 10 to 18 cm long (not including the petioles).

*Stipules:* None.

*Petioles:* Long, stout. Generally glabrous or with a few widely scattered hairs. Size: 50 to 100 mm long by 2 to 3 mm thick. Color: Yellow green RHS 144A, except upper surface turning to red R.H.S. 46B to R.H.S. 46A where exposed to full sun.

Buds: Conical, sharply acute, with imbricate scales. Terminal buds are 4–6 mm long by 2–3 mm wide and are moderately pubescent. Lateral buds are 3–4 mm long by 2 mm wide and are sparsely pubscent. Color of dormant buds in winter is brown R.H.S. 200A to greyed-purple R.H.S. 187A.

Flowers: Campanulate, corymbose, apetalous, 5 mm. Only observed in the initially discovered tree, appears to be the same as the species.

Fruit: A samara, 2.5 to 3.5 cm. long by 8 to 10 mm. wide, borne in pairs joined at the seed end. Wings slightly divergent. Glabrous. Only observed in the initially discovered tree, appears to be the same as the species.

Growth rate: Very slow, dwarf tree.

Distinguishing Characteristics

My new tree exhibits an extremely compact growth habit and has a dwarf to semi-dwarf growth rate. In observations as of this time, trees of my new cultivar have grown less than half the rate of typical *Acer saccharum* seedlings. In addition, trees of my new variety have short internode length. In observations as of this time, the internode length of the trees of my new variety has been observed to be less than one-third as long as the internode length of typical *Acer saccharum* seedlings. In addition, my new variety has a narrow upright shape with a straight, dominant leader.

Observations

The height of one year old nursery plants of my new cultivar and one year old *Acer saccharum* seedlings growing under the same conditions in rows adjacent to rows containing the trees of my new variety were compared. That is, the heights were averaged for twenty such trees of each variety. The height of these trees of my new cultivar averaged thirty-six percent of the height of the seedling trees. The height and width of the oldest propagule of my new cultivar, aged thirteen years, was compared to the average height and width of three typical *Acer saccharum* trees of the same age growing in the same plot. The height of this new cultivar tree was forty-eight percent of the height of these three comparison *Acer saccharum* trees and the width of the new cultivar tree was thirty-five percent of the width of these comparison trees. The results of these comparisons are set forth in the table below.

The internode length comparisons set forth in the table below were calculated by averaging the mid-stem internode length of twenty one-year old trees of *Acer saccharum* seedlings and twenty trees of my new variety growing under the same growing conditions. The internode length of my new cultivar on average, as determined from these observations of these groups of twenty trees, was twenty-six percent of the internode length of the seedlings.

| | New Cultivar | *Acer saccharum* Seedlings |
|---|---|---|
| Height, 1 year | 83 cm | 228 cm |
| Height, 13 years | 5.2 meters | 10.8 meters |
| Width, 13 years | 1.8 meters | 5.1 meters |
| Internode length | 35 mm | 137 mm |

I claim:

1. A new and distinct variety of sugar maple tree substantially as herein shown and described, characterized particularly as to novelty by a compact growth habit, a short internode length, and a narrow upright shape with a straight, dominant leader.

* * * * *